United States Patent

Gaster et al.

[11] Patent Number: 5,889,022
[45] Date of Patent: Mar. 30, 1999

[54] INDOLE, INDOLINE AND QUINOLINE DERIVATIVES WITH 5HT$_{1D}$ (ANTI-DEPRESSIVE) ACTIVITY

[75] Inventors: Laramie Mary Gaster, Bishop's Stortford; Paul Adrian Wyman, Epping, both of England

[73] Assignee: SmithKline Beecham, p.l.c., Middlesex, England

[21] Appl. No.: 663,291

[22] PCT Filed: Dec. 16, 1994

[86] PCT No.: PCT/EP94/04181

§ 371 Date: Jun. 20, 1996

§ 102(e) Date: Jun. 20, 1996

[87] PCT Pub. No.: WO95/17398

PCT Pub. Date: Jun. 29, 1995

[30] Foreign Application Priority Data

Dec. 21, 1993 [GB] United Kingdom .................. 9326009
Feb. 22, 1994 [GB] United Kingdom .................. 9403317
Aug. 25, 1994 [GB] United Kingdom .................. 9417187

[51] Int. Cl.$^6$ .................. A61K 31/47; C07D 215/12
[52] U.S. Cl. .................. 514/314; 514/364; 514/210; 514/211; 514/213; 514/224.2; 514/230.5; 514/373; 514/375; 514/412; 540/202; 540/476; 540/552; 540/583; 546/114; 546/115; 546/168; 546/152; 546/131; 546/217; 546/500
[58] Field of Search .................. 514/314, 364, 514/210, 211, 213, 224.2, 230.5, 373, 375, 412; 546/168, 114, 115; 548/131, 152, 217, 500; 540/202, 476, 352, 583

[56] References Cited

U.S. PATENT DOCUMENTS 5,354,766 10/1994 Naka et al. .................. 514/364

FOREIGN PATENT DOCUMENTS 0 533 268  3/1993  European Pat. Off. .
0 520 423  12/1993  European Pat. Off. .

Primary Examiner—Joseph McKane
Assistant Examiner—Richard S. Myers, Jr.
Attorney, Agent, or Firm—Stephen Venetianer; Edward T. Lentz

[57] ABSTRACT

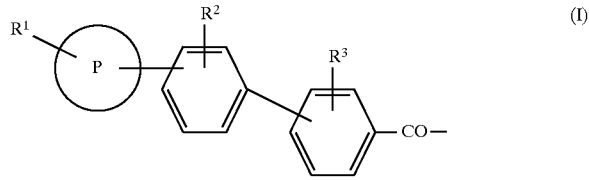

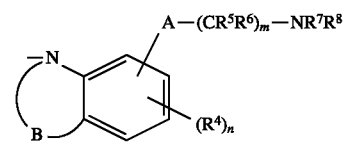

Novel indole, indoline and quinoline derivatives of formula (I) processes for their preparation, pharmaceutical compositions containing them, and their use in medicine is disclosed. A structurally distinct class of compounds have now been discovered and have been found to exhibit 5HT$_{1-D}$ antagonist activity. In a first aspect, the present invention therefore provides a compound of formula (I) or a salt thereof, in which P is a 5–7-membered heterocyclic ring containing 1 to 3 heteroatoms selected from oxygen, nitrogen or sulphur, A, B, m, R$^1$–R$^8$ are defined in the application.

9 Claims, No Drawings

INDOLE, INDOLINE AND QUINOLINE DERIVATIVES WITH 5HT$_{1D}$ (ANTI-DEPRESSIVE) ACTIVITY

This is a National Stage filing under 37 U.S.C. § 371 of PCT/EP94/04181, filed Dec. 12, 1994.

The present invention relates to novel indole, indoline and quinoline derivatives, processes for their preparation, and pharmaceutical compositions containing them.

EPA 0 533 266/7/8 disclose a series of benzanilide derivatives which are said to possess 5HT$_{1D}$ receptor antagonist activity. These compounds are alleged to be of use in the treatment of various CNS disorders such as depression.

A structurally distinct class of compounds have now been discovered and have been found to exhibit 5HT$_{1D}$ antagonist activity. In a first aspect, the present invention therefore provides a compound of formula (I) or a salt thereof:

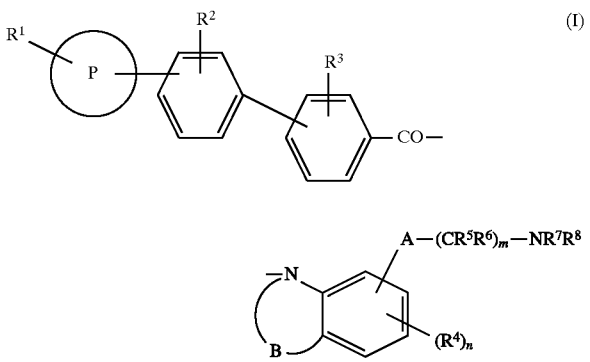

in which

P is a 5–7-membered heterocyclic ring containing 1 to 3 heteroatoms selected from oxygen, nitrogen or sulphur;

$R^1$, $R^2$ and $R^3$ are independently hydrogen, halogen, $C_{1-6}$alkyl, $C_{3-6}$cycloalkyl, $C_{3-6}$cycloalkenyl, $C_{1-6}$alkoxy, acyl, aryl, acyloxy, hydroxy, nitro, trifluoromethyl, cyano, $CO_2R^9$, $CONR^{10}R^{11}$, $NR^{10}R^{11}$ where $R^9$, $R^{10}$ and $R^{11}$ are independently hydrogen or $C_{1-6}$alkyl;

$R^4$ is hydrogen, halogen, hydroxy, $C_{1-6}$alkyl or $C_{1-6}$alkoxy;

$R^5$ and $R^6$ are independently hydrogen or $C_{1-6}$alkyl;

$R^7$ and $R^8$ are independently hydrogen, $C_{1-6}$alkyl, aralkyl, or together with the nitrogen atom to which they are attached form an optionally substituted 5- to 7-membered heterocyclic ring containing one or two heteroatoms selected from oxygen, nitrogen or sulphur;

A is oxygen, $S(O)_n$ where n is 0, 1 or 2, or A is $NR^{12}$ where $R^{12}$ is hydrogen or $C_{1-6}$alkyl, or A is $CR^5=CR^6$ or $CR^5R^6$ where $R^5$ and $R^6$ are independently hydrogen or $C_{1-6}$alkyl;

m is 1 to 4;

n is 1 or 2; and

B is $(CR^{13}R^{14})_q$ where q is 2, 3 or 4 and $R^{13}$ and $R^{14}$ are independently hydrogen or $C_{1-6}$alkyl or B is $(CR^{13}R^{14})_r$—D where r is 0, 1, 2 or 3 and D is oxygen, sulphur or $CR^{13}=CR^{14}$.

$C_{1-6}$alkyl groups, whether alone or as part of another group, may be straight chain or branched.

Suitably $R^1$, $R^2$ and $R^3$ are independently hydrogen, halogen, $C_{1-6}$alkyl, $C_{3-6}$cycloalkyl, $C_{3-6}$cycloalkenyl, $C_{1-6}$alkoxy, acyl, aryl, acyloxy, hydroxy, nitro, trifluoromethyl, cyano, $CO_2R^9$, $CONR^{10}R^{11}$, $NR^{10}R^{11}$ where $R^9$, $R^{10}$ and $R^{11}$ are independently hydrogen or $C_{1-6}$alkyl. Preferably $R^1$ and $R^2$ are both $C_{1-6}$alkyl, particularly methyl. Preferably $R^3$ is hydrogen.

Suitably P is a 5 to 7-membered heterocyclic ring containing 1 to 3 heteroatoms selected from oxygen, nitrogen or sulphur. Examples of suitable heterocyclic rings include thienyl, furyl, pyrrolyl, triazolyl, diazolyl, imnidazolyl, oxadiazolyl, isothiazolyl, isoxazolyl, thiadiazolyl, pyxidyl, pyrimidyl and pyrazinyl. The heterocyclic rings can be linked to the remainder of the molecule via a carbon atom or, when present, a nitrogen atom. Preferably P is oxadiazolyl.

Suitably $R^4$ is hydrogen, halogen, hydroxy, $C_{1-6}$alkyl or $C_{1-6}$alkoxy. Preferably $R^4$ is $C_{1-6}$alkoxy such as methoxy. Preferably n is 1.

Suitably $R^5$ and $R^6$ are independently hydrogen or $C_{1-6}$alkyl. Preferably $R^5$ and $R^6$ are both hydrogen.

Suitably $R^7$ and $R^8$ are independently hydrogen, $C_{1-6}$alkyl or aralkyl such as benzyl. Examples of $R^7$ and $R^8$ heterocyclic rings include morpholine, piperazine and piperidine. Optional substituents for such rings include $C_{1-6}$alkyl. Preferably $R^7$ and $R^8$ are both $C_{1-6}$alkyl, in particular methyl.

Suitably A oxygen, $S(O)_n$ where n is 0, 1 or 2, or A is $NR^{12}$ where $R^{12}$ is hydrogen or $C_{1-6}$alkyl, or A is $CR^5=CR^6$ or $CR^5R^6$ where $R^5$ and $R^6$ are independently hydrogen or $C_{1-6}$alkyl. Preferably A is oxygen.

Suitably B is $(CR^{13}R^{14})_q$ where q is 2, 3 or 4 and $R^{13}$ and $R^{14}$ are independently hydrogen or $C_{1-6}$alkyl or B is $(CR^{13}R^{14})_r$—D where r is 0, 1, 2 or 3 and D is oxygen, sulphur or $CR^{13}=CR^{14}$. Preferably $R^{13}$ and $R^{14}$ are both hydrogen such that the group B forms part of an indole, indoline or tetrahydroquinoline ring.

Suitably m is 1 to 4, preferably m is 1 or 2.

The groups —A(CR$^5$R$^6$)$_m$NR$^7$R$^8$ and $R^4$ can be attached to the phenyl ring at any suitable position. Preferably the group —A(CR$^5$R$^6$)$_m$NR$^7$R$^8$ is meta to the amide linkage. The groups $R^1$, $R^2$ and $R^3$ can also be attached at any suitable position.

Particularly preferred compounds include:

5-Chloro-2,3-dihydro-6-(2-dimethylaminoethoxy)-1-[4-(2-methyl-1,2,4-oxadiazol-3-yl)phenyl)benzoyl]1-H-indole, 2,3-Dihydro-6-(3-dimethylaminopropyl)-5-methoxy-1-[4-(2-methyl-1,2,4-oxadiazol-3-yl)phenyl)benzoyl]1-H-indole, 2,3-dihydro-6-(2-(dimethylaminoethoxy)-5-methoxy-1-[4-(2-methyl-4-(5-methyl-1,2,4oxadiazol-3-yl)phenyl)benzoyl]-1H-indole, and 6-(2-(dimethylaminoethoxy)-5-methoxy-1-[4-(2-methyl-4-(5-methyl-1,2,4-oxadiazol-3-yl)phenyl)benzoyl]-1H-indole,

[7-(2-Dimethylaminoethoxy)-6-methoxy-3,4-dihydro-2H-quinolin-1-yl]-[2'-methyl-4'(5-methyl-1,2,4-oxadiazol-3-yl)biphenyl-4yl]methanone,

[7-(3-Dimethylaminopropyl)-6-methoxy-3,4-dihydro-2H-quinolin-1-yl]-[2'-methyl-4'-(5-methyl-1,2,4-oxadiazol-3-yl)biphenyl-4-yl]methanone, or pharmaceutically acceptable salts thereof.

Preferred salts of the compounds of formula (I) are pharmaceutically acceptable salts. These include acid addition salts such as hydrochlorides, hydrobromides, phosphates, acetates, fumarates, maleates, tartrates, citrates, oxalates, methanesulphonates and p-toluenesulphonates.

Certain compounds of formula (I) are capable of existing in stereoisomeric forms. It will be understood that the invention encompasses all geometric and optical isomers of the compounds of formula (I) and the mixtures thereof including racemates. Tautomers of compounds of formula (I) also form an aspect of the invention.

In a further aspect the present invention provides a process for the preparation of a compound of formula (I) which comprises:

coupling a compound of formula (II):

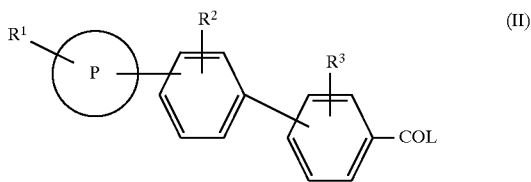

in which P, $R^1$, $R^2$ and $R^3$ are as defined in formula (I) and L is a leaving group with a compound of formula (III):

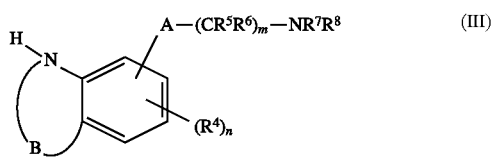

in which A, B, $R^5$, $R^6$, $R^7$, $R^8$, m and n are as defined in formula (I), and optionally thereafter in any order:
  converting a compound of formula (I) into another compound of formula (I)
  forming a pharmaceutically acceptable salt.

Suitable activated carboxylic acid derivatives of formula (II) include acyl halides and acid anhydrides. Activated compounds of formula (II) can also be prepared by reaction of the corresponding carboxylic acid with a coupling reagent such as carbonyldiimidazole, dicyclohexylcarbodiimide or diphenylphosphorylazole. Preferably the group L is halo, particularly chloro.

A compound of formula (II) is typically reacted with a compound of formula (III) in an inert organic solvent such as DMF, THF or dichloromethane at ambient or elevated temperature in the presence of a base such as triethylamine, pyridine or an aqueous alkali metal hydroxide. When the compound of formula (II) is an indole, t-BuOK can also be used in an inert solvent such as THF.

Compounds of formula (II) can be prepared from a compound of formula (IV):

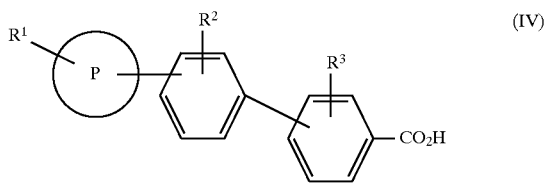

in which P, $R^1$, $R^2$ and $R^3$ are as defined in formula (I) using standard procedures. For example acid chlorides can be prepared by reaction with phosphorous pentachloride, oxalyl chloride or thionyl chloride. Acid anhydrides can be prepared by reaction with a suitable acid anhydride, for example trifluoroacetic anhydride.

Intermediate compounds of formula (IV) can be prepared using standard procedures such as those outlined in EPA 533266/7/8. Intermediate compounds of formula (III) are commercially available or can be prepared using standard procedures.

It will be appreciated by those skilled in the art that it may be necessary to protect certain reactive substituents during some of the above procedures. Suitable protecting groups and methods for their attachment and removal are conventional in the art of organic chemistry, such as those described in Greene T. W. 'Protective groups in organic synthesis' New York, Wiley (1981).

For example, secondary amines can be protected as benzyl, benzyloxycarbonyl or t-butyl dicarbonate derivatives. These groups can be removed by conventional procedures.

Carboxylic acid groups can be protected as esters. Aldehyde or ketone groups can be protected as acetals, ketals, thioacetals or thioketals. Deprotection is achieved using standard conditions.

Certain compounds of formula (I) can be converted into further compounds of formula (1). For example compounds in which $R^7$ and $R^8$ are both hydrogen or one of $R^7$ or $R^8$ is hydrogen and the other is $C_{1-6}$alkyl can be converted to compounds in which $R^7$ and $R^8$ are both $C_{1-6}$alkyl using standard alkylation techniques.

Novel intermediates of formulae (II), (III) and (IV) also form part of the invention.

$5HT_{1D}$ Antagonists, and in particular the compounds of the present invention, may therefore be of use in the treatment of CNS disorders such as mood disorders, including depression, seasonal effective disorder and dysthymia; anxiety disorders, including generalised anxiety, panic disorder, agoraphobia, social phobia, obsessive compulsive disorder and post-traumatic stress disorder; memory disorders, including dementia, amnestic disorders and age-associated memory impairment; and disorders of eating behaviors, including anorexia nervosa and bulimia nervosa. Other CNS disorders include Parkinson's disease, dementia in Parkinson's disease, neuroleptic-induced Parkinsonism and tardive dyskinesias, as well as other psychiatric disorders.

$5HT_{1D}$ Antagonists, and in particular compounds of the present invention, may also be of use in the treatment of endocrine disorders such as hyperprolactinaemia, in the treatment of vasospasm (particularly in the cerebral vasculature) and hypertension, as well as disorders in the gastrointestinal tract where changes in motility and secretion are involved. They may also be of use in the treatment of sexual dysfunction.

Therefore, the present invention, provides a compound of general formula (I) or a physiologically acceptable salt or solvate thereof for use in therapy.

The present invention also provides a compound of general formula (I) or a physiologically acceptable salt or solvate thereof for use in the treatment of the aforementioned disorders.

In another aspect the invention provides the use of a compound of general formula (I) or a pharmaceutically acceptable salt or solvate thereof for the manufacture of a medicament for the treatment of the aforementioned disorders.

In a further aspect the invention provides a method of treating the aforementioned disorders which comprises administering an effective amount to a patient in need of such treatment of a compound of general formula (I) or a pharmaceutically acceptable salt or solvate thereof.

In particular the invention provides a compound of general formula (I) or a physiologically acceptable salt or solvate thereof for use in the treatment or prophylaxis of depression.

It will be appreciated by those skilled in the art that the compounds according to the invention may advantageously be used in conjunction with one or more other therapeutic agents, for instance, different antidepressant agents.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavorings or colorants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three a day. Such therapy may extend for a number of weeks or months.

The following Examples illustrate the preparation of compounds of the invention.

DESCRIPTION 1

2-Chloro-5-nitroanisole (D1)

The title compound was prepared from 2-methoxy-4-nitroaniline (15.0 g, 0.089 mol) using the procedure of Bonilha, J. B. S. et al., Tetrahedron 1993, 49 (15), 3053–64. Yield 8.61 g, (51%).

$^1$H NMR (CDCl$_3$) δ: 7.80–7.87 (m, 2H), 7.50 (d, 1H), 4.00 (s, 3H).

DESCRIPTION 2

2-Chloro-5-nitrophenol (D2)

The title compound was synthesised from 2-chloro-5-nitroanisole (6.0 g, 0.032 mol) using the method described in Tetrahedron, 1993, 49 (15), 3053–64. Yield 5.08 g, (91%).

$^1$H NMR (CDCl$_3$) δ: 7.90 (d, 1H), 7.77 (dd, 1H), 7.5 (d, 1H), 5.90 (s, 1H).

DESCRIPTION 3

4-Chloro-3-(2-dimethylaminoethoxy)nitroaniline (D3)

2-Chloro-5-nitrophenol (350 mg, 0.002 mol ) in DME (25 ml) was treated with dimethylaminoethyl chloride HCl (640 mg) and K$_2$CO$_3$ (5 g) and the mixture was heated under reflux for 19 hours. The reaction was allowed to cool to room temperature, then the solvent removed in vacuo. The residue was taken up in water and extracted with EtOAc. The organic layers were combined, dried (Na$_2$SO$_4$) and concentrated in vacuo to give a yellow oil, which crystallised on standing. Purification by flash column chromatography, eluting with EtOAc gave the title compound (343 mg, 70% ).

$^1$H NMR (CDCl$_3$) δ: 7.81 (m, 2H), 7.60 (m, 1H), 4.21 (t, 3H), 2.88 (t, 2H), 2.40 (s, 6H).

DESCRIPTION 4

4-Chloro-3-(2-dimethylaminoethoxy)aniline (D4)

To 4-chloro-3-(2-dimethylaminoethoxy)nitrobenzene (1.5 g 0.006 mol) in EtOH (25 ml) at 60° C., was added SnCl$_2$ (4.2 g) in concentrated hydrochloric acid (7.6 ml) dropwise. The mixture was then heated under reflux for 30 mins and after cooling to room temperature, diluted with water (50 ml), and basified by addition of 40% aq. sodium hydroxide. The mixture was extracted into CH$_2$Cl$_2$ and the combined organic layers, dried (Na$_2$SO$_4$) and concentrated in vacuo to give the title compound as a brown oil (1.22 g, 93%).

$^1$H NMR (CDCl$_3$) δ: 7.08 (d, 1H), 6.24–6.18 (m, 2H), 4.03 (t, 2H), 3.78 (brs, 2H), 2.77 (t, 2H), 2.34 (s, 6H).

DESCRIPTION 5

N-[4-Chloro-3-(2-dimethylaminoethoxy)phenyl] aminoacetaldehyde dimethyl acetal (D5)

To a suspension of 4-chloro-3-(2-dimethylaminoethoxy) aniline (1.22 g, 0.006 mol) in MeOH (30 ml) containing dimethoxyethanal in MTBE (1.76 g, 0.17 mol) and glacial acetic acid (1.71 g) was added sodium cyanoborohydride (1.78 g, 0.03 mol ) portionwise at 0° C. The reaction was left to stir at room temperature for 1 hour, and then 10% aq. NaOH was added and the mixture was extracted with CH$_2$Cl$_2$. The combined organic layers were dried (Na$_2$SO$_4$), and concentrated in vacuo to give a brown oil. Purification by FCC, eluting with CH$_2$Cl$_2$ gave the title compound (1.49 g, 87%)

$^1$H NMR (CDCl$_3$) δ: 7.10 (d, 1H), 6.21–6.12 (m, 2H), 4.53 (t, 1H), 4.10 (t, 2H), 3.92–3.87 (m, 1H ), 3.40 (s, 6H), 3.21 (t, 2H), 2.80 (t, 2H), 2.38 (s, 6H).

DESCRIPTION 6

5-Chloro-6-(2-dimethylaminoethoxy)-1H-indole (D6)

A solution of the product from description 5, (0.61 g, 0.002 mol) in TFA (2.6 ml) at 0° C., was treated with TFA (2.6 ml) under an argon atmosphere. More TFA (3.7 ml) was added and the reaction was heated to reflux for 48 h. The solution was evaporated to dryness and the residue taken up in EtOAc. The extract was dried ($Na_2SO_4$) and concentrated in vacuo to leave a brown oil which was dissolved in MeOH (10 ml), treated with $K_2CO_3$ (1 g) and then stirred at room temperature for 3 h The mixture was concentrated in vacuo, and then the residue treated with water and extracted with EtOAc. The solution was dried ($Na_2SO_4$)and concentrated in vacuo to give the title compound as a brown solid (0.37 g, 76%)

$^1$H NMR ($CDCl_3$) δ: 8.32 (brs, 1H), 7.6 (s, 1H), 7.12 (m, 1H), 6.92 (s, 1H), 6.47 (m, 1H), 4.11 (t, 2H), 2.81 (t, 2H), 2.40 (s, 6H).

DESCRIPTION 7

5-Chloro-2,3-dihydro-6-(2-dimethylaminoethoxy)-1H-indole (D7)

The product from description 6 (0.2 g, 0.008 mol) in glacial acetic acid (5 ml) was treated with sodium cyanoborohydride (0.25 g, 0.004 mol) at room temperature with stirring for 1 h. The mixture was diluted with water and basified with 10% aq. NaOH. The product was extracted into $CH_2Cl_2$, and the combined extracts dried ($Na_2SO_4$) and concentrated in vacuo to give the title compound as a brown oil (0.21 g, 100%)

$^1$H NMR ($CDCl_3$) 6: 7.04 (s, 1H), 6.30 (s, 1H), 5.85 (bs, 1H), 4.04 (t, 2H), 3.59 (t, 2h), 2.98 (t, 2H), 2.79 (t, 2H), 2.38 (s, 6H).

DESCRIPTION 8

2-Chloro-5-nitro-N,N-dimethylcinnamide (D8)

A stirred suspension of 2-chloro-5-nitrocinnamic acid (20 g, 0.088 mol) in thionyl chloride (100 ml) was heated to reflux for 3 h, then concentrated in vacuo to leave the acid chloride as a beige solid. This was dissolved in a mixture of $CH_2Cl_2$ (100 ml) and dry THF (30 ml), then added dropwise to a stirred suspension of dimethylamine hydrochloride (9.8 g, 0.12 mol) and pyridine (24 ml) at −20° C. under argon. The reaction mixture was then allowed to warm to room temperature and stirred for 1.5 h. The solvent was removed in vacuo and the residue redissolved in $CH_2Cl_2$. The resulting solution was washed with 10% aq. $Na_2CO_3$ solution, 1M HCl acid, then water, then dried ($Na_2SO_4$) and concentrated in vacuo to give the title compound as a beige solid (22.2 g, 99%).

$^1$H NMR ($CDCl_3$) δ: 8.46 (d, 1H), 8.12 (dd, 1H), 8.00 (d, 1H), 7.60 (d, 1H), 7.04 (d, 1H), 3.23 (s, 3H), 3.11 (s, 3H).

DESCRIPTION 9

2-Methoxy-5-nitro-N,N-dimethylcinnamide (D9)

Sodium (2.1 g, 0.0093 mol) was added carefully to MeOH (120 ml) at room temperature under argon and when all the metal had reacted, the solution was concentrated in vacuo to leave sodium methoxide as a white solid. This was treated with dry DMF (120 ml) and the resulting semi-suspension cooled to 0° C. A solution of the product from description 8 (15.9 g, 0.062 mol) in dry DMF (80 ml) was added dropwise. After 40mins, the reaction mixture was poured into 1M HCl acid/ice mixture (2000 ml), to give a white precipitate, which was filtered off and dissolved in chloroform. The solution was washed well with water, dried ($Na_2SO_4$) and concentrated to give the title compound as a pale yellow solid (15.5 g, 100%).

$^1$H NMR ($CDCl_3$) δ: 8.40 (d, 1H), 8.21 (dd, 1H), 7.92 (d, 1H), 7.05 (d, 1H), 6.98 (d, 1H), 4.00 (s, 3H), 3.21 (s, 3H), 3.10, (s, 3H).

DESCRIPTION 10

3-(5-Amino-2-methoxy)phenyl-N,N-dimethylpropionamide (D10)

A suspension of the product from description 9 (6 g, 0.024 mol) in EtOH (100 ml) was hydrogenated at atmospheric pressure and temperature for 18 h. over 10% palladium on carbon (0.7 g). The catalyst was removed by filtration through kieselguhr, and the filtrate was concentrated in vacuo to give the title compound as a brown oil (5.47 g, 100%)

$^1$H NMR ($CDCl_3$) δ: 6.68 (d, 1H), 6.58–6.49 (m, 2H), 3.75 (s, 3H), 3.48 (br s, 2H), 2.97 (d, 6H) 2.89–2.82 (m, 2H), 2.59–2.50 (m, 2H).

DESCRIPTION 11

3-(Dimethylaminopropyl)-4-methoxyaniline (D11)

To a suspension of sodium borohydride(2.72 g, 0.07 mol) in dry THF (75 ml) at 0° C. under argon was added $BF_3OEt_2$ (11.8 ml) dropwise. The mixture was left to stir for 1 h, and then a solution of the product from description 10 (5.32 g, 0.024 mol) in THF (75 ml) was added and the solution was heated under reflux for 2 h. After cooling to room temperature, aq. $Na_2CO_3$ was added dropwise and then the solvent was removed in vacuo. The residue was taken up in a mixture of EtOH (21 ml) and 5N HCl (21 ml), and the mixture was heated under reflux for 1 h. The solvent was removed in vacuo, and the residue treated with saturated aq. $K_2CO_3$, until a pH of 8 was reached. The suspension was then extracted with EtOAc and the combined organic layers dried ($Na_2SO_4$) and concentrated in vacuo to give the title compound as a brown oil (3.46 g, 71%).

$^1$H NMR ($CDCl_3$) δ: 6.68( d, 1H), 6.54–6.48 (m, 2H), 3.72 (s, 3H), 3.68(br s, 2H) 2.58 (t, 2H), 2.32(t, 2H), 2.27(s, 6H), 1.82–1.68 (m, 2H).

DESCRIPTION 12

2,3-Dihydro-6-(dimethylaminopropyl)-5-methoxy-1H-indole (D12)

The title compound was prepared from the compound of Description 11 using methodology described in Descriptions 14,15 and 16.

$^1$H NMR ($CDCl_3$) d: 6.65 (s, 1H), 6.40 (s, 1H), 5.85 (brs, 1H), 3.68 (s, 3H), 3.42 (t, 2H), 2.90 (t, 2H), 2.70 (t, 2H), 2.58–2.42 (m, 8H), 1.84 (m, 2H).

DESCRIPTION 13

2-(2-Dimethylaminoethoxy)-4-nitroanisole (D13)

A stirred solution of 2-methoxy-5-nitrophenol (10 g, 0.059 mole) in 1,2-dimethoxyethane (80 ml) was treated with saturated aqueous potassium carbonate solution (32 ml) followed by 2-dimethylaminoethyl chloride hydrochloride (8.2 g, 0.057 mole) and heated under reflux for 17 hours. A further quantity of 2-dimethylaminoethyl chloride hydrochloride (4.0 g, 0.029 mole) was added and reflux was continued for 18 hours. The mixture was then concentrated in vacuo and the residue treated with 10% $Na_2CO_3$ solution (100 ml) and extracted with ethyl acetate (2×100 ml). The combined extract was dried (Na$_2$SO$_4$) and concentrated in vacuo to afford the title compound as a yellow solid (11.8 g, 83%).

$^1$H NMR (CDCl$_3$) δ: 7.92 (dd, 1H), 7.77 (d, 1H), 6.91 (d, 1H), 4.18 (t, 2H), 3.96 (s, 3H), 2.82 (t, 2H), 2.37 (s, 6H).

DESCRIPTION 14

3-(2-Dimethylaminoethoxy)-4-methoxyaniline (D14)

A solution of 2-(2-dimethylaminoethoxy)-4-nitroanisole (D13, 11.8 g, 0.049 mole) in ethanol (200 ml) was hydrogenated over 10% Pd-C (1 g) at atmospheric temperature and pressure. The catalyst was filtered off through kieselguhr and the filtrate concentrated in vacuo to afford the title compound as a beige solid (10.3 g, 100%).

$^1$H NMR (CDCl$_3$) δ: 6.71 (d, 1H), 6.33 (d, 1H), 6.24 (dd, 1H), 4.07 (t, 2H), 3.78 (s, 3H), 3.46 (br s, 2H), 2.76 (t, 2H), 2.33 (s, 6H).

DESCRIPTION 15

N-[3-(Dimethylaminoethoxy)-4-methoxyphenyl] aminoacetaldehyde dimethyl acetal (D15)

A solution of 3-(2-dimethylaminoethoxy)-4-methoxyaniline (D14, 5.7 g, 0.027 mole) in ethanol (120 ml) was treated with a solution of 2,2-dimethoxyacetaldehyde in methyl tert-butyl ether (9.5 g of approx. 40% solution, 0.036 mole) and kept at room temperature for 16 hours. The solution was then hydrogenated over 10% Pd-C (0.6 g) at atmospheric pressure and temperature for 7 hours. The catalyst was removed by filtration through kieselguhr and the filtrate concentrated in vacuo. The residue was dissolved in ethyl acetate (100 ml), washed twice with water (2×60 ml), then dried (Na$_2$SO$_4$) and concentrated in vacuo. The residue was chromatographed on silica gel eluting with 5% methanol/chloroform to afford the title compound as a red oil (5.4 g, 67%).

$^1$H NMR (CDCl$_3$) δ: 6.75(d,1H), 6.30(d,1H), 6.19(dd, 1H), 4.56(t,1H), 4.08(t,2H), 3.78(s,3H), 3.61(br t,1H), 3.42 (s,6H), 3.20(t,2H), 2.78(t,2H), 2.34(s,6H).

DESCRIPTION 16

6-(2-Dimethylaminoethoxy)-5-methoxy-1H-indole (D16)

A stirred solution of N-[3-(2-dimethylaminoethoxy)-4-methoxyphenyl]aminoacetaldehyde dimethyl acetal (D15), 5.3 g, 0.018 mole) in trifluoroacetic acid (22 ml) at −5° C. under argon was treated dropwise over 40 minutes with trifluoroacetic anhydride (22 ml). After a further 30 minutes the dark solution was treated with more trifluoroacetic acid (33 ml) and then heated under reflux for 7 hours. The solution was concentrated in vacuo and the residue basified with 10% Na$_2$CO$_3$ solution and extracted with ethyl acetate. The extract was dried (Na$_2$SO$_4$), concentrated in vacuo and the residue dissolved in methanol (100 ml), treated with potassium carbonate (10 g) and stirred at room temperature for 3 hours. The mixture was concentrated in vacuo, the residue treated with water (60 ml) and extracted with ethyl acetate (2×70 ml). The combined extract was dried (Na$_2$SO$_4$) and concentrated in vacuo to afford the title compound as a brown solid (3.5 g, 83%).

$^1$H NMR (d$^6$DMSO) δ: 7.14(t,1H), 7.05(s,1H), 6.96(s, 1H), 6.27(br t,1H), 4.03(t,2H), 3.75(s,3H), 3.45(br s), 2.70 (t,2H), 2.27(s,6H).

DESCRIPTION 17

2,3-Dihydro-6-(2-dimethylaminoethoxy)-5-methoxy-1H-indole (D17)

A stirred solution of 6-(2-dimethylaminoethoxy)-5-methoxy-1H-indole (D16, 0.50 g, 2.1 mmole) in glacial acetic acid (10 ml) at room temperature was treated portionwise over 15 minutes with sodium cyanoborohydride (0.25 g, 4 mmole). After 2 hours the solution was diluted with water (50 ml), basified by addition of Na$_2$CO$_3$ and then extracted with ethyl acetate (2×50 ml). The combined extract was dried (Na$_2$SO$_4$), and concentrated in vacuo to leave the title compound as a brown oil (0.37 g, 73%).

$^1$H NMR (CDCl$_3$) δ: 6.75(s,1H), 6.37(s,1H), 4.05(t,2H), 3.90(br s,1H), 3.77(s,3H), 3.52(t,2H), 2.96(t,2H), 2.73(t, 2H), 2.32(s,6H).

DESCRIPTION 18

7-(2-Dimethylaminoethoxy)-6-methoxyquinoline (D18)

3-(2-Dimethylaminoethoxy)-4-methoxyaniline (D14, 200 mg) was treated with glycerol (133 mg) and iodine (5 mg) and to this stirring mixture was added dropwise, concentrated sulphuric acid (267 mg). After the initial exothermic reaction had subsided, the mixture was heated at 180° C. for 1.5 hr. The reaction mixture was cooled and partitioned between 40% aqueous sodium hydroxide and ethyl acetate, the organic phase was dried (Na$_2$SO$_4$) and the solvent evaporated under reduced pressure to leave the title compound as a brown oil (19 mg, 51%).

$^1$H NMR (CDCl$_3$) δ: 8.72 (dd, 1H), 8.00 (d, 1H), 7.44 (s, 1H), 7.3–7.24(m, 1H), 706 (s, 1H), 4.30 (t, 2H), 4.0 (s, 3H), 2.9 (t, 2H), 2.39 (s, 6H).

DESCRIPTION 19

7-(2-Dimethylaminoethoxy)-6-methoxy-1,2,3,4-tetrahydroquinoline (D19)

A solution of 7-(2-dimethylaminoethoxy)-6-methoxyquinoline (D18) (119 mg) in ethanol (20 ml) was hydrogenated over PtO$_2$ (170 mg) at ambient temperature and 50 p.s.i. for 2 hr. After removal of the catalyst, the filtrate was evaporated under reduced pressure to give the title compound as a pale yellow solid (118 mg, 98%).

$^1$H NMR (CDCl$_3$) δ: 6.53 (s, 1H), 6.21 (s, 1H), 4.45–4.35 (m, 2H), 3.75 (s, 3H), 3.5–3.39 (m, 2H), 3.25 (t, 2H), 2.95 (s, 6H), 2.70 (t, 2H), 2.0–1.82 (m, 2H).

DESCRIPTION 20

7-(3-Dimethylaminopropyl)-6-methoxyquinoline (D20)

Following the procedure outlined in description 18, 3-(dimethylaminopropyl)-4-methoxyaniline (D11) (300 mg) was converted to the title compound (203 mg, 58%).

$^1$H NMR (CDCl$_3$) δ: 8.75 (dd, 1H), 8.02 (d, 1H), 7.85 (s, 1H), 7.35–7.28 (m, 1H), 7.02 (s, 1H), 3.94 (s, 3H), 2.82 (t, 2H), 2.39 (t, 2H), 2.25 (s, 6H), 1.96–1.79 (m, 2H).

DESCRIPTION 21

7-(3-Dimethylaminopropyl)-6-methoxy-1,2,3,4-tetrahydroquinoline (D21)

Following the procedure outlined in description 19, 7-(3-dimethylaminopropyl)-6-methoxyquinoline (D20) (200 mg)

was converted to the title compound as a pale yellow semi solid. (192 mg, 94%).

$^1$H NMR (CDCl$_3$) δ: 6.5 (s, 1H), 6.32 (s, 1H), 3.71 (s, 3H), 3.3–3.16 (m, 2H), 2.85–2.3 (m, 12 H), 2.04–1.75 (m, 4H).

EXAMPLE 1

5-Chloro-2,3-dihydro-6-(2-dimethylaminoethoxy)-1-[4-(2-methyl-1,2,4-oxadiazol-3-yl)phenyl)benzoyl]-1H-indole To a suspension of 4-(2-methyl-4-(5-methyl-1,2,4-oxadiazol-3-yl)phenyl)benzoic acid (EP 0533268A) (0.24 g, 0.0009 mol) in CH$_2$Cl$_2$ (10 ml), under an argon atmosphere, was added oxalyl chloride (0.08 ml), and 5 drops of DMF. After 1 h at room temperature a homogeneous solution was obtained and the solvent was removed in vacuo. The residue was redissolved in CH$_2$Cl$_2$ (5 ml) and the solution added dropwise to a solution of the product from description 7 (0.21 g, 0.0009 mol) in CH$_2$Cl$_2$ (5 ml) containing Et$_3$N (0.24 ml). The mixture was stirred at room temperature for 19 h. Saturated aqueous Na$_2$CO$_3$ solution was added to the mixture, which was then extracted with CH$_2$Cl$_2$. The organic extracts were combined, dried (Na$_2$SO$_4$) and concentrated in vacuo to give the title compound as a brown solid. Purification by FCC, eluting with CH$_2$Cl$_2$ gave the title compound (0.21 g, 54%).

$^1$H NMR (CDCl$_3$) δ: 8.02–7.92 (m, 3H) 7.93 (d, 2H), 7.62 (d, 2H), 7.43 (d, 1H), 7.02 (s, 1H), 4.20–4.13 (m, 4H), 3.10 (t, 2H), 2.80 (brs, 2H), 2.69 (s, 3H), 2.37 (s, 9H).

EXAMPLE 2

2,3-Dihydro-6-(3-dimethylaminopropyl)-5-methoxy-1-[4-(2-methyl-1,2,4-oxadiazol-3-yl)phenyl)benzoyl]1-H-indole.

The title compound was prepared by the method described in Example 1 from 4-(2-methyl-4-(5-methyl-1,2,4-oxadiazol-3-yl)phenyl)benzoic acid (EP 0533268A) (0.14 g, 0.0005 mol) and the product from description 12 (0.12 g, 0.0005 mol). Yield 38%

$^1$H NMR (CDCl$_3$) δ: 8.09–7.93 (m, 3H), 7.64 (d, 2H), 7.44 (d, 2H), 7.36 (d, 1H), 6.75 (s, 1H), 4.20–4.14 (m, 2H), 3.80 (s, 3H), 3.15 (t, 2H), 2.69 (s, 3H), 2.40–2.50 (b,10H), 2.35 (s, 3H), 2.05–1.10 (m, 2H).

EXAMPLE 3

2,3-Dihydro-6-(2-dimethylaminoethoxy)-5-methoxy-1-[4-(2-methyl-4-(5-methyl-1,2,4-oxadiazol-3-yl)phenyl)benzoyl]-1H-indole A stirred suspension of 4-(2-methyl-4-(5-methyl-1,2,4-oxadiazol-3-yl)phenyl)benzoic acid (EP 0533268A) (165 mg, 0.55 mmole) in thionyl chloride (5 ml) was heated under reflux for 2 hours. The solution was then concentrated in vacuo to leave the acid chloride as a yellow solid. This was dissolved in THF (5 ml) and added to a stirred solution of 2,3-dihydro-6-(2-dimethylaminoethoxy)-5-methoxy-1H-indole (D17, 118 mg, 0.50 mmole) in a mixture of water (5 ml) and THF (5 ml) containing sodium hydroxide (45 mg, 1.1 mmole). The mixture was kept at room temperature for 18 h, then concentrated to approx. 50% volume, diluted with 10% Na$_2$CO$_3$ solution (20 ml) and extracted with ethyl acetate (2×20 ml). The combined extract was dried (Na$_2$SO$_4$), concentrated in vacuo and the residue chromatographed on silica gel eluting with 5% methanol/chloroform. Crystallisation from ether afforded the title compound as a white solid (55 mg, 21%) mp 140°–141° C.

1H NMR (d$^6$DMSO at 80° C.) δ: 7.96(s,1H), 7.90(dd, 1H), 7.65(d,2H), 7.50(d,2H), 7.43(d,1H), 7.35(v br,lH), 6.94 (s,1H), 4.09(t,2H), 3.93(br t,2H), 3.76(s,3H), 3.00–3.10(m, 2H), 2.68(s,3H), 2.61(t,2H), 2.36(s,3H), 2.22(s,6H).

EXAMPLE 4

6-(2-Dimethylaminoethoxy)-5-methoxy-1-[4-(2-methyl-4-(5-methyl-1,2,4-oxadiazol-3-yl)phenyl) benzoyl]-1H-indole A stirred suspension of 4-(2-methyl-4-(5-methyl-1,2,4-oxadiazol-3-yl)phenyl)benzoic acid (EP 0533268A) (165 mg, 0.55 mmole) in thionyl chloride (5 ml) was heated under reflux for 2 hours. The solution was then concentrated in vacuo to leave the acid chloride as a yellow solid.

A stirred solution of 6-(2-dimethylaminoethoxy)-5-methoxy-1H-indole (D16, 118 mg, 0.50 mmole) in THF (10 ml) under argon was treated with potassium tert-butoxide (56 mg, 0.50 mmole) and kept at room temperature for 20 minutes, then treated with a solution of the above acid chloride (0.55 mmole) in THF (5 ml). The mixture was stirred at room temperature for 18 h then concentrated in vacuo. The residue was treated with 10% Na$_2$CO$_3$ solution (20 ml) and extracted with ethyl acetate (2×20 ml). The combined extract was dried (Na$_2$SO$_4$) and concentrated in vacuo. The residue was chromatographed on silica gel eluting with 5% methanol/chloroform and the material obtained crystallised from ether to afford the title compound as a white solid (60 mg, 23%) mp 130°–131° C.

$^1$H NMR (CDCl$_3$) δ: 8.07(s,1H), 7.95(s,1H), 7.90(d,1H), 7.74(d,2H), 7.44(d,2H), 7.31(d,1H), 7.17(d,1H), 6.98(s,1H), 6.47(d,1H), 4.14(t,2H), 3.85(s,3H), 2.79(t,2H), 2.60(s,3H), 2.30(s,9H).

EXAMPLE 5

[7-(2-Dimethylaminoethoxy)-6-methoxy-3,4-dihydro-2H-quinolin-1-yl]-[2'-methyl-4'(5-methyl-1,2,4-oxadiazol-3-yl)biphenyl-4-yl]methanone A stirred suspension of 4-(2-methyl-4-(5-methyl-1,2,4-oxadiazol-3-yl)phenyl)benzoic acid (EP 0533268A1) (138 mg, 0.47mmol) in thionyl chloride (4 ml) was heated under reflux for 2 hr. The solution was then concentrated under reduced pressure to leave the acid chloride as a yellow solid. This was dissolved in dichloromethane (10 ml) and treated with triethylamine (0.13 ml) followed by a solution of 7-(2-dimethylaminoethoxy)-6-methoxy-1,2,3,4-tetrahydroquinoline (D19) (118 mg, 0.47 mmol) in dichloromethane (10 ml). The mixture was stirred at room temperature for 3 hr under argon, then evaporated under reduced pressure, and the residue partitioned between saturated aqueous Na$_2$CO$_3$ solution and ethyl acetate. The organic phase was dried (Na$_2$SO$_4$) and evaporated under reduced pressure, and the residue purified on a silica gel column eluting with methanol and dichloromethane, to give the title compound as a white foam (108 mg, 44%). Conversion to the oxalate salt gave a white solid, mp 139°–141° C.

$^1$H NMR (CDCl$_3$) (Free base) δ: 7.99 (s, 1H), 7.91 (d, 1H), 7.51–7.41 (m, 2H), 7.35–7.25 (m, 3H), 6.65 (s, 1H), 6.4 (brs, 1H), 3.94 (t, 2H), 3.81 (s, 3H), 3.69–3.56 (m, 3H), 2.82 (t, 2H), 2.69 (s, 3H), 2.59 (t, 2H), 2.30 (s, 3H), 2.21 (s, 6H), 2.14–1.97 (m, 2H).

EXAMPLE 6

[7-(3-Dimethylaminopropyl)-6-methoxy-3,4-dihydro-2H-quinolin1-yl]-[2'-methyl-4'-(5-methyl-1,2,4-oxadiazol-3-yl)biphenyl-4-yl]methanone (E6)

The title compound was prepared by the method described in Example 5 from 4-(2-methyl-4-(5-methyl-1,2, 4-oxadiazol-3-yl)phenyl)benzoic acid (215 mg; 0.734 mmol) and 7-(3-dimethylamninopropyl)-6-methoxy-1,2,3,4-tetrahydroquinoline (D21) (182 mg; 0.734 mmol). Yield 13%. Conversion to the oxalate salt gave an off-white powder, m.p. 169°–171° C.

$^1$H NMR (CDCl$_3$) δ: 7.97 (s, 1H), 7.92 (d, 1H), 7.44 (d, 2H), 7.35–7.2 (m, 3H), 6.6 (s, 2H), 3.93 (t, 2H), 3.79 (s, 3H), 2.82 (t, 2H), 2.68 (s, 3H), 2.44–1.98 (m, 15 H), 1.57–1.36 (m, 2H).

We claim:

1. A compound of formula (1) or a salt thereof:

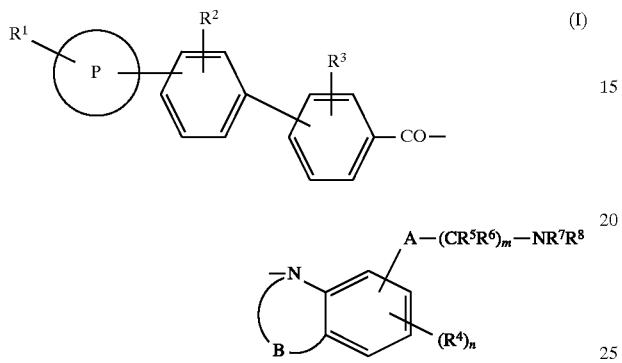

in which
P is a 5–7-membered heterocyclic ring containing 1 to 3 heteroatoms selected from oxygen, nitrogen or sulphur;
$R^1$, $R^2$ and $R^3$ are independently hydrogen, halogen, $C_{1-6}$alkyl, $C_{3-6}$cycloalkyl, $C_{3-6}$cycloalkenyl, $C_{1-6}$alkoxy, acyl, aryl, acyloxy, hydroxy, nitro, trifluoromethyl, cyano, $CO_2R^9$, $CONR^{10}R^1$ 1, $NR^{10}R^{11}$ where $R^9$, $R^{10}$ and $R^{11}$ are independent $C_{1-6}$alkyl;
$R^4$ is hydrogen, halogen, hydroxy, $C_{1-6}$alkyl or $C_{1-6}$alkoxy;
$R^5$ and $R^6$ are independently hydrogen or $C_{1-6}$alkyl;
$R^7$ and $R^8$ are independently hydrogen, $C_{1-6}$alkyl, aralkyl, or together with the nitrogen atom to which they are attached form an optionally substituted 5- to 7-membered heterocyclic ring containing one or two heteroatoms selected from oxygen, nitrogen or sulphur;
A is oxygen, $S(O)_n$ where n is 0, 1 or 2, or A is $NR^{12}$ where $R^{12}$ is hydrogen or $C_{1-6}$alkyl, or A is $CR^5=CR^6$ or $CR^5R^6$ where $R^5$ and $R^6$ are independently hydrogen or $C_{1-6}$alkyl;
m is 1 to 4;
n is 1 or 2; and
B is $(CR^{13}R^{14})_q$ where q is 2, 3 or 4 and $R^{13}$ and $R^{14}$ are independently hydrogen or $C_{1-6}$alkyl or B is $(CR^{13}R^{14})_r$—D where r is 0, 1, 2 or 3 and D is oxygen, sulphur or $CR^{13}=CR^{14}$.

2. A compound according to claim 1 in which $R^1$ and $R^2$ are $C_{1-6}$alkyl.

3. A compound according to claim 1 in which $R^3$ is hydrogen.

4. A compound according to claim 1 in which P is oxadiazol.

5. A compound according to claim 1 in which $R^4$ is $C_{1-6}$alkoxy.

6. A compound according to claim 1 in which $R^5$ is hydrogen.

7. A compound according to claim 1 selected from the group consisting of
5-Chloro-2,3-dihydro-6-(2-Dimethylaminoethoxy)-1-[4-(2-methyl-1,2,4-oxadiazol-3-yl)phenyl)benzoyl]1-H-indole,
2,3-Dihydro-6-(3-dimethylaminopropyl)-5-methoxy-1-[4-(2-methyl-1,2,4-oxadiazol-3-yl)phenyl)benzoyl]1-H-indole,
2,3-dihydro-6-(2-(dimethylaminoethoxy)-5-methoxy-1-[4-(2-methyl-4-(5-methyl-1,2,4-oxadiazol-3-yl)phenyl)benzoyl]-1H-indole, and
6-(2-(dimethylaminoethoxy)-5-methoxy-1-[4-(2-methyl-4-(5-methyl-1,2,4-oxadiazol-3-yl)phenyl)benzoyl]-1H-indole,
[7-(2-Dimethylaminoethoxy)-6-methoxy-3,4-dihydro-2H-quinolin-1-yl]-[2'-methyl-4'(5-methyl-1,2,4-oxadiazol-3-yl)biphenyl-4-yl]methanone, and
[7-(3-Dimethylaminopropyl)-6-methoxy-3,4-dihydro-2H-quinolin-1-yl]-[2'-methyl-4'-(5-methyl-1,2,4-oxadiazol-3-yl)biphenyl-4-yl]methanone,
or pharmaceutically acceptable salts thereof.

8. A process for the preparation of a compound of formula (I) or a pharmaceutically acceptable salt which comprises:
coupling a compound of formula (II):

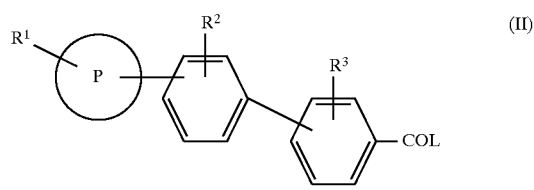

in which P, $R^1$, $R^2$ and $R^3$ are as defined in formula (I) and L is a leaving group with a compound of formula (III):

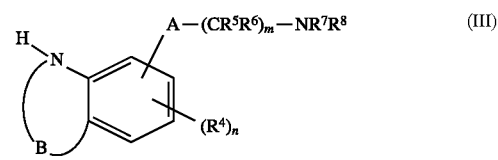

in which A, B, $R^5$, $R^6$, $R^7$, $R^8$, m and n are as defined in formula (I).

9. A pharmaceutical composition which comprises a compound according to claim 1 in association with a pharmaceutically acceptable carrier or excipient.

* * * * *